US012702281B2

(12) United States Patent
Yanagawa et al.

(10) Patent No.: US 12,702,281 B2
(45) Date of Patent: Aug. 11, 2026

(54) ENDOLUMINAL DEVICE SYSTEM, CONTROL METHOD OF CONTROLLING ENDOLUMINAL DEVICE, AND STORAGE MEDIUM STORING PROGRAM FOR CONTROLLING ENDOLUMINAL DEVICE

(71) Applicant: OLYMPUS MEDICAL SYSTEMS CORP., Tokyo (JP)

(72) Inventors: Ryota Yanagawa, Hachioji (JP); Kosuke Kishi, Mitaka (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 126 days.

(21) Appl. No.: 18/440,050

(22) Filed: Feb. 13, 2024

(65) Prior Publication Data

US 2024/0180405 A1 Jun. 6, 2024

Related U.S. Application Data

(63) Continuation of application No. PCT/JP2022/038580, filed on Oct. 17, 2022.

(Continued)

(51) Int. Cl.
*A61B 1/005* (2006.01)
*A61B 1/00* (2006.01)

(52) U.S. Cl.
CPC ........ *A61B 1/0057* (2013.01); *A61B 1/00097* (2022.02)

(58) Field of Classification Search
CPC .......................... A61B 1/0057; A61B 1/00097
See application file for complete search history.

(56) References Cited

U.S. PATENT DOCUMENTS 5,938,588 A 8/1999 Grabover et al.
9,214,139 B2 12/2015 Nakayama (Continued)

FOREIGN PATENT DOCUMENTS

JP H04-176430 A 6/1992
JP H0622904 A 2/1994

(Continued)

OTHER PUBLICATIONS

US Office Action dated Aug. 18, 2025 received in U.S. Appl. No. 18/809,672.

(Continued)

*Primary Examiner* — Jonathan R Messmore
(74) *Attorney, Agent, or Firm* — Scully, Scott, Murphy & Presser, P.C.

(57) ABSTRACT

A manipulation detection portion detects a first manipulation on the basis of a motion of an object in contact with a contact detection device. A drive control portion performs a shape control process of changing a shape of at least a part of an endoluminal device on the basis of the first manipulation. The manipulation detection portion detects a second manipulation on the basis of the motion of the object while the object is continuously in contact with the contact detection device after the detection of the first manipulation starts. The drive control portion performs a control process of maintaining a shape in which at least a part of the endoluminal device is changed on the basis of the second manipulation.

20 Claims, 12 Drawing Sheets

Related U.S. Application Data

(60) Provisional application No. 63/310,756, filed on Feb. 16, 2022, provisional application No. 63/281,796, filed on Nov. 22, 2021.

(56) References Cited

U.S. PATENT DOCUMENTS

| | | | | |
|---|---|---|---|---|
| 10,666,854 | B2 | 5/2020 | Furuhata | |
| 2002/0062063 | A1 | 5/2002 | Ogura et al. | |
| 2002/0103418 | A1 | 8/2002 | Maeda et al. | |
| 2004/0138530 | A1 | 7/2004 | Kawai et al. | |
| 2007/0100201 | A1 | 5/2007 | Komiya et al. | |
| 2016/0128773 | A1 | 5/2016 | Ogawa et al. | |
| 2017/0080581 | A1 | 3/2017 | Iida et al. | |
| 2017/0143438 | A1 | 5/2017 | Komuro | |
| 2017/0209227 | A1 | 7/2017 | Yoshimura | |
| 2018/0095580 | A1* | 4/2018 | Yi | A61B 1/00097 |
| 2019/0303000 | A1 | 10/2019 | Furuhata | |
| 2020/0093353 | A1* | 3/2020 | Tezuka | A61B 5/065 |
| 2020/0100857 | A1 | 4/2020 | Nakashima | |
| 2021/0000329 | A1* | 1/2021 | Tezuka | A61B 1/00078 |
| 2021/0146539 | A1 | 5/2021 | Tanaka et al. | |
| 2021/0259790 | A1 | 8/2021 | Kaiser | |
| 2021/0307591 | A1 | 10/2021 | OuYang | |
| 2022/0197487 | A1* | 6/2022 | Koo | G06F 3/0488 |
| 2022/0409013 | A1* | 12/2022 | Kambe | A61B 1/008 |
| 2024/0179394 | A1 | 5/2024 | Oslie et al. | |

FOREIGN PATENT DOCUMENTS

| | | | |
|---|---|---|---|
| JP | H06-269398 | A | 9/1994 |
| JP | H06-269401 | A | 9/1994 |
| JP | 2000300511 | A | 10/2000 |
| JP | 3233373 | B2 | 11/2001 |
| JP | 2002224016 | A | 8/2002 |
| JP | 2003235790 | A | 8/2003 |
| JP | 2004041538 | A | 2/2004 |
| JP | 3549434 | B2 | 8/2004 |
| JP | 2007125180 | A | 5/2007 |
| JP | 2010158566 | A | 7/2010 |
| JP | 2012-020028 | A | 2/2012 |
| JP | 2013-027466 | A | 2/2013 |
| JP | 2015024038 | A | 2/2015 |
| JP | 2019-000351 | A | 1/2019 |
| JP | 2019-170853 | A | 10/2019 |
| JP | 2019-180488 | A | 10/2019 |
| JP | 2021-151468 | A | 9/2021 |
| WO | 2004086957 | A2 | 10/2004 |
| WO | 2018225121 | A1 | 12/2018 |
| WO | 2019/107226 | A1 | 6/2019 |
| WO | 2021/145424 | A1 | 7/2021 |
| WO | 2021145410 | A1 | 7/2021 |
| WO | 2021145411 | A1 | 7/2021 |

OTHER PUBLICATIONS

International Search Report dated May 16, 2023 received in PCT/JP2023/007294.

International Search Report dated Apr. 18, 2023 received in PCT/JP2023/007332.

International Search Report dated May 9, 2023 received in PCT/JP2023/007334.

International Search Report dated Apr. 25, 2023 received in PCT/JP2023/007304.

International Search Report dated Dec. 20, 2022 received in PCT/JP2022/038580.

International Search Report dated Dec. 27, 2022 received in PCT/JP2022/039138.

US Office Action dated Nov. 17, 2025 received in U.S. Appl. No. 18/584,645.

US Office Action dated Mar. 9, 2026 received in U.S. Appl. No. 18/809,730.

US Office Action dated May 7, 2026 received in U.S. Appl. No. 18/809,780.

* cited by examiner

ENDOLUMINAL DEVICE SYSTEM, CONTROL METHOD OF CONTROLLING ENDOLUMINAL DEVICE, AND STORAGE MEDIUM STORING PROGRAM FOR CONTROLLING ENDOLUMINAL DEVICE

CROSS-REFERENCE TO RELATED APPLICATIONS

The present application is a continuation application based on PCT Patent Application No. PCT/JP2022/038580, filed on Oct. 17, 2022, of which priority is claimed on U.S. Patent Provisional Application No. 63/281,796, filed Nov. 22, 2021, and U.S. Patent Provisional Application No. 63/310,756, filed Feb. 16, 2022, the entire contents of which are hereby incorporated by reference.

BACKGROUND

Field of the Invention

The present disclosure relates to technology for controlling an operation of an endoluminal device such as an endoscope.

Description of Related Art

In an endoscopic examination, an elongated insertion portion with flexibility is inserted into a patient's body. A bending portion capable of being bent upward, downward, left, or right is provided on a distal end portion of a flexible insertion portion and the bending portion can freely bend its shape in accordance with a manipulation of an endoscope manipulation portion by a doctor. During the examination, the doctor manipulates an angle knob of the endoscope manipulation portion to orient a distal end of the bending portion in a desired direction, and then performs a lock manipulation on an angle fixing lever of the endoscope manipulation portion to fix the bending portion in a bent state, and images a lesion using an imaging portion. When imaging of the lesion is completed and the doctor performs an unlock manipulation on the angle fixing lever, the bending portion gradually returns to its original straight shape from the bent shape due to an elastic force.

In recent years, an electric endoscope for bending the bending portion of the endoscope with an actuator has been developed for the purpose of efficiently observing and treating lesions. U.S. patent Ser. No. 10/666,854 (hereinafter referee to as Patent Document 1) discloses technology for bending the bending portion in a stroke direction according to a manipulation of stroking a touch panel with a finger. Patent Document 1 also discloses that when the touch panel is tapped with a finger, the bending portion is bent so that a tap position is centered in an image display region, and the shape of the bending portion is fixed (angle-locked).

In comparison with a process in which a doctor manipulates an angle knob and an angle fixing lever of an endoscope manipulation portion and bends a bending portion, a process in which a doctor can control a bending operation on a bending portion by manipulating a touch panel is expected to significantly reduce the fatigue of the doctor during the examination. Therefore, there is a desire to develop technology for enabling a user to easily control the operation of an endoluminal device such as an endoscope using a contact detection device such as a touch panel.

SUMMARY

The present disclosure has been made in view of the above-described circumstances and an objective of the present disclosure is to provide technology for enabling a user to easily control an operation of an endoluminal device.

To solve the above-described problems, according to a certain aspect of the present invention, there is provided an endoluminal device system including: an endoluminal device configured to be inserted into a lumen; a contact detection device configured to detect contact of an object; and one second manipulation or more processors having hardware. The one or more processors detect a first manipulation on the basis of a motion of the object in contact with the contact detection device, perform a shape control process of changing a shape of at least a part of the endoluminal device on the basis of the first manipulation, detect a second manipulation on the basis of the motion of the object while the object is continuously in contact with the contact detection device after the detection of the first manipulation starts, and perform a first control process of maintaining a shape in which at least a part of the endoluminal device is changed on the basis of the second manipulation.

Another aspect of the present invention relates to a control method for an endoluminal device in an endoluminal device system including an endoluminal device inserted into a lumen and a contact detection device configured to detect contact of an object. The control method includes detecting a first manipulation on the basis of a motion of the object in contact with the contact detection device; performing a shape control process of changing a shape of at least a part of the endoluminal device on the basis of the first manipulation; detecting a second manipulation on the basis of the motion of the object while the object is continuously in contact with the contact detection device after the detection of the first manipulation starts; and performing a first control process of maintaining a shape in which at least a part of the endoluminal device is changed on the basis of the second manipulation.

Yet another aspect of the present invention relates to a computer program storage medium storing a program for controlling an endoluminal device inserted into a lumen. The storage medium stores the program for causing the computer to implement: a function of detecting a first manipulation on the basis of a motion of the object in contact with the contact detection device; a function of performing a shape control process of changing a shape of at least a part of the endoluminal device on the basis of the first manipulation; a function of detecting a second manipulation on the basis of the motion of the object while the object is continuously in contact with the contact detection device after the detection of the first manipulation starts; and a function of performing a first control process of maintaining a shape in which at least a part of the endoluminal device is changed on the basis of the second manipulation.

Also, any combination of the above constituent elements, and expressions of the present disclosure that are compatible between a method, a device, a system, a recording medium, a computer program, and the like are also effective as an aspect of the present disclosure.

An endoluminal device system, a control method for an endoluminal device, and a computer program storage medium storing a program for controlling the endoluminal device according to the present invention can enable a user to easily control an operation of an endoluminal device.

BRIEF DESCRIPTION OF THE DRAWINGS

FIG. 6 is a diagram showing a functional block of a control device.

DETAILED DESCRIPTION

Figure 1:
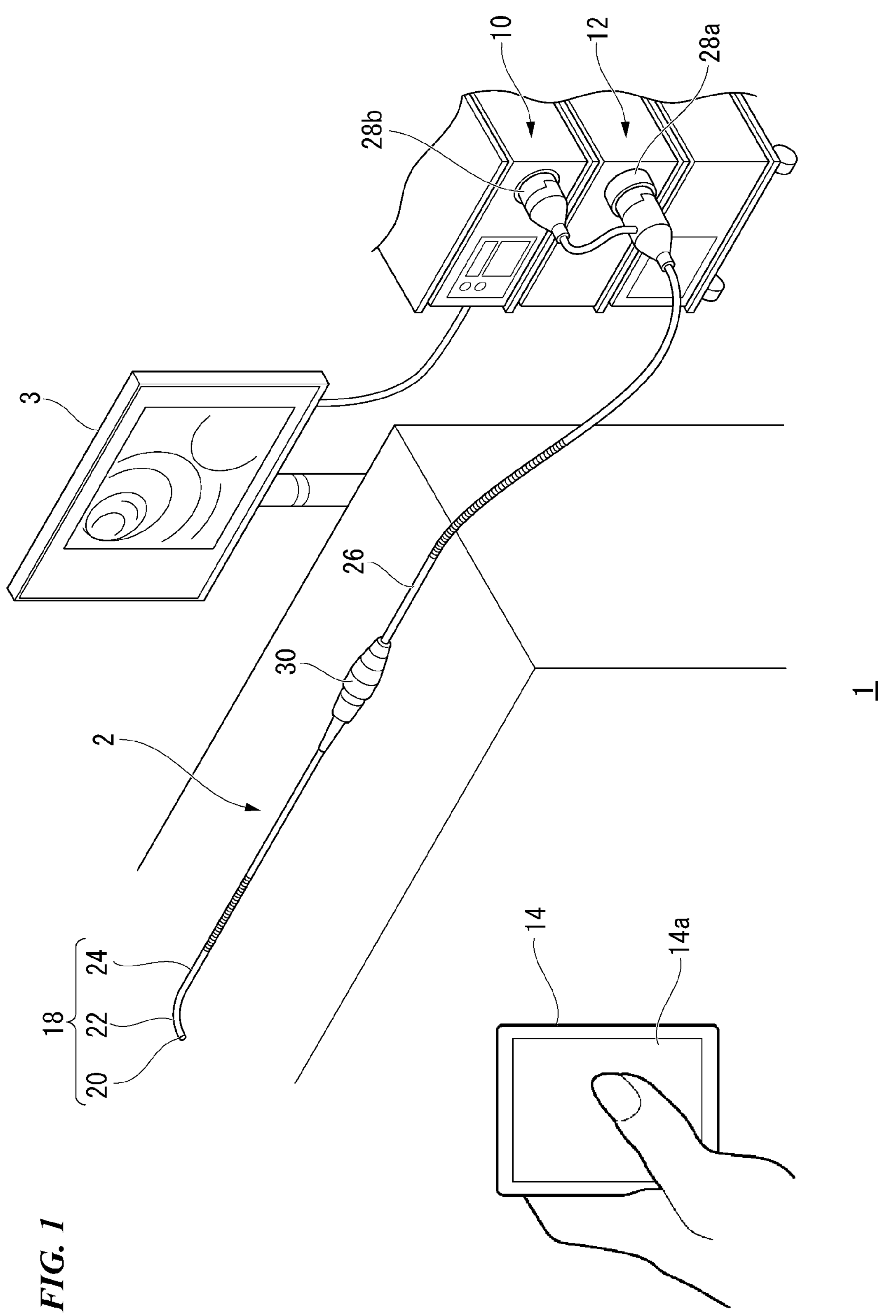
FIG. 1 is a diagram showing a configuration of an endoluminal device system of an embodiment.

FIG. 1 shows a configuration of an endoluminal device system 1 of an embodiment. The endoluminal device system 1 is a medical system provided in a medical facility such as a hospital and includes an endoluminal device 2, a display device 3, a control device 10, a drive device 12, and a contact detection device 14. The endoluminal device 2 is a medical device that is inserted into a patient's lumen to observe and/or treat lesions. The endoluminal device 2 of the embodiment is an endoscope and the endoluminal device system 1 may be provided in an endoscopic examination room.

The endoluminal device 2 includes an insertion portion 18, an extracorporeal soft portion 26, a connection portion 30 for connecting the insertion portion 18 and the extracorporeal soft portion 26, a connection portion 28*a* connected to the drive device 12, and a connection portion 28*b* connected to the control device 10. The insertion portion 18 is an elongated long member that can be inserted into the patient's lumen and has a distal end portion 20, a bending portion 22 whose shape can be changed, and an intracorporeal soft portion 24 connected to a proximal end of the bending portion 22. The intracorporeal soft portion 24 and the extracorporeal soft portion 26 are soft members that are easily bent, and can be deformed by receiving an external force. The connection portion 30 connects the intracorporeal soft portion 24 and the extracorporeal soft portion 26 rotatably about a rotation axis extending in a longitudinal direction. Therefore, even if a user who is a doctor rotates the intracorporeal soft portion 24, the extracorporeal soft portion 26 does not rotate. The endoluminal device 2 is connected to the drive device 12 by the connection portion 28*a* and connected to the control device by the connection portion 28*b*.

The distal end portion 20 includes an opening for advancing and retracting the treatment tool, an illumination window for emitting illumination light transmitted by the light guide into the lumen, and an imaging portion configured to image the lumen in prescribed cycles, and outputs an imaging signal to the control device 10. The imaging portion includes a solid-state image sensor (for example, a CCD image sensor or a CMOS image sensor) for converting incident light into an electrical signal. Also, when the endoluminal device 2 is a device other than an endoscope, various types of end effectors may be mounted on the distal end portion 20.

Figure 2:
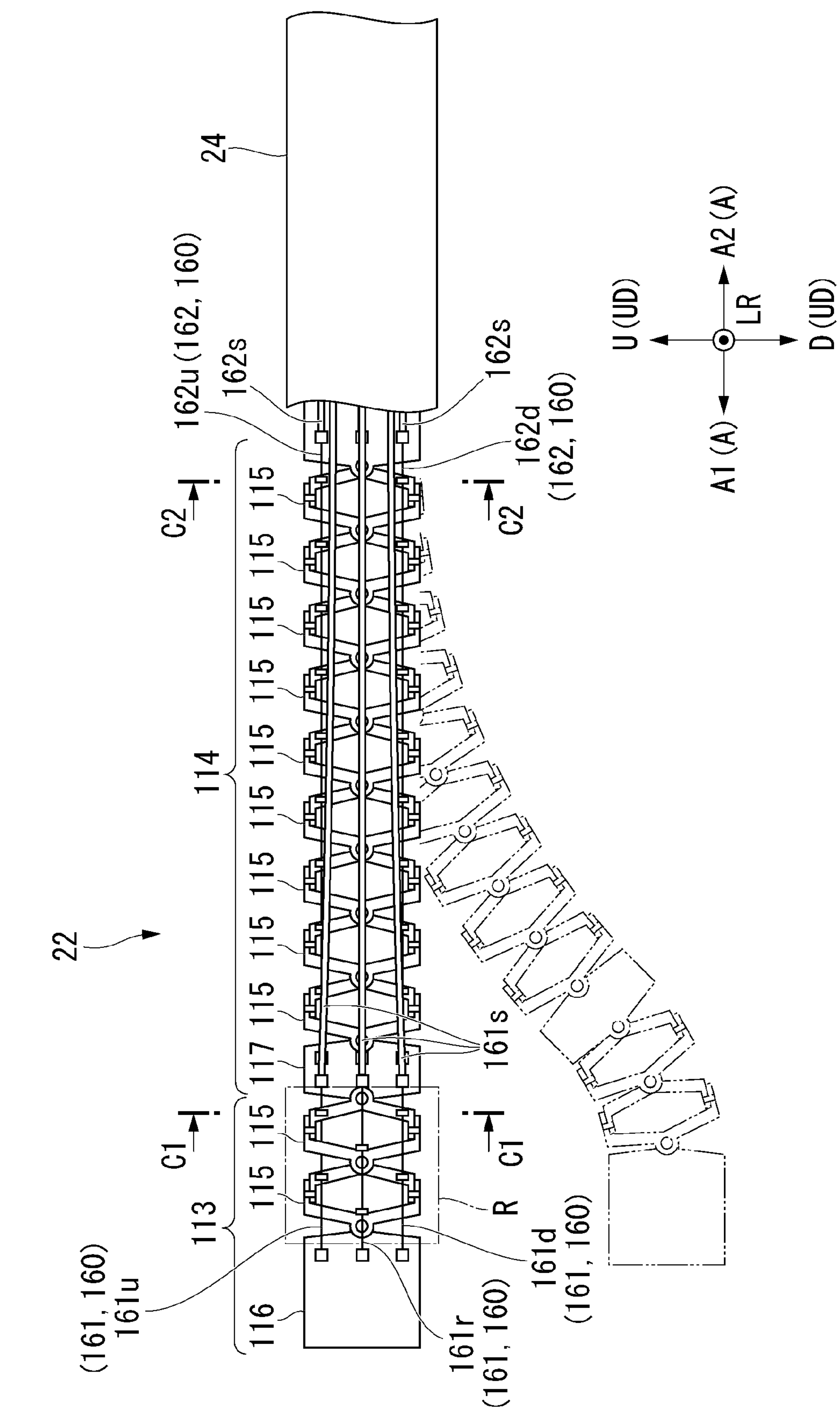
FIG. 2 is a diagram showing a cross-sectional internal configuration of a bending portion.

FIG. 2 shows a cross-sectional internal configuration of the bending portion 22. The bending portion 22 includes a first bending portion 113 on a distal end side, a second bending portion 114 on a proximal end side, and an outer sheath 118 (see FIG. 3) that protects an internal structure of the bending portion 22. The first bending portion 113 and the second bending portion 114 can be bent in different directions. In the embodiment, in order to express a relative positional relationship in the longitudinal direction A of the endoluminal device 2, the side close to the distal end portion 20 is referred to as a "distal end side (A1)" and the side close to the connection portion 28 is sometimes referred to as a "proximal end side (A2)."

The first bending portion 113 includes a plurality of joint rings (also referred to as "bending pieces") 115 and a first distal end portion 116 connected to the leading joint ring 115. The plurality of joint rings 115 and the first distal end portion 116 are connected inside of the outer sheath 118 in the longitudinal direction A. The shapes and number of the joint rings 115 provided in the first bending portion 113 are not limited to the shapes and number of the joint rings 115 shown in FIG. 2.

Figure 3:
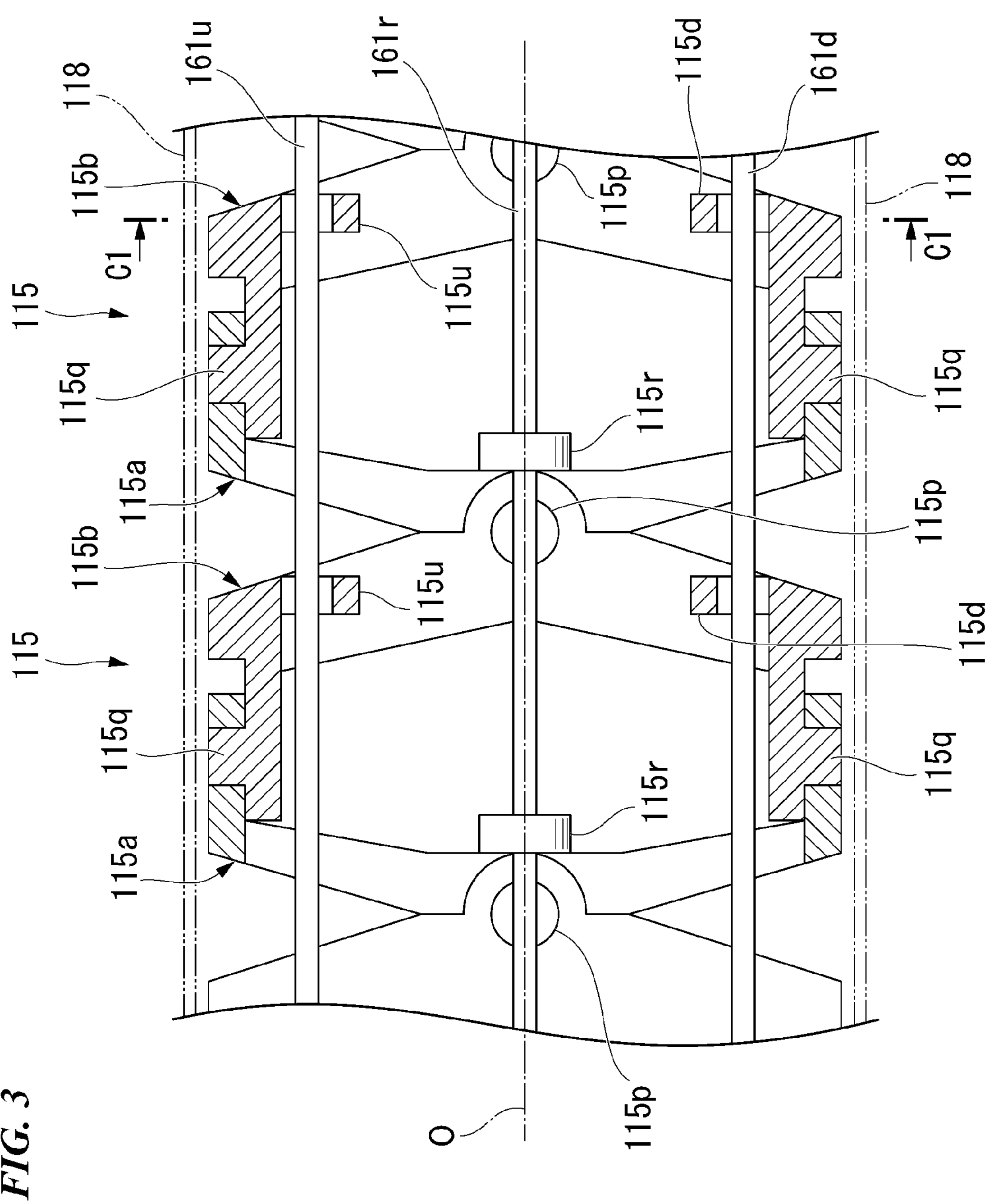
FIG. 3 is an enlarged view of joint rings.

FIG. 3 shows an enlarged view of the joint rings 115 in a region R shown in FIG. 2. The joint rings 115 are short cylindrical members formed of a metal and have a first joint ring 115*a* on the distal end side and a second joint ring 115*b* on the proximal end side. The first joint ring 115*a* and the second joint ring 115*b* are rotationally connected by a first rotation pin 115*p* in an upward/downward direction (also referred to as a "UD direction") perpendicular to the longitudinal direction A.

The plurality of joint rings 115 are connected so that the internal spaces of adjacent joint rings 115 are continuously connected. In the adjacent joint rings 115, the second joint ring 115*b* of the joint rings 115 of the distal end side and the first joint ring 115*a* of the joint rings 115 of the proximal end side are rotationally connected by a second rotation pin 115*q* in a left/right direction (also referred to as an "LR direction") perpendicular to the longitudinal direction A and the upward/downward direction (the UD direction). The first joint ring 115*a* and the second joint ring 115*b* are alternately connected by the first rotation pin 115*p* and the second rotation pin 115*q* and the first bending portion 113 can be bent in a desired direction.

Figure 4:
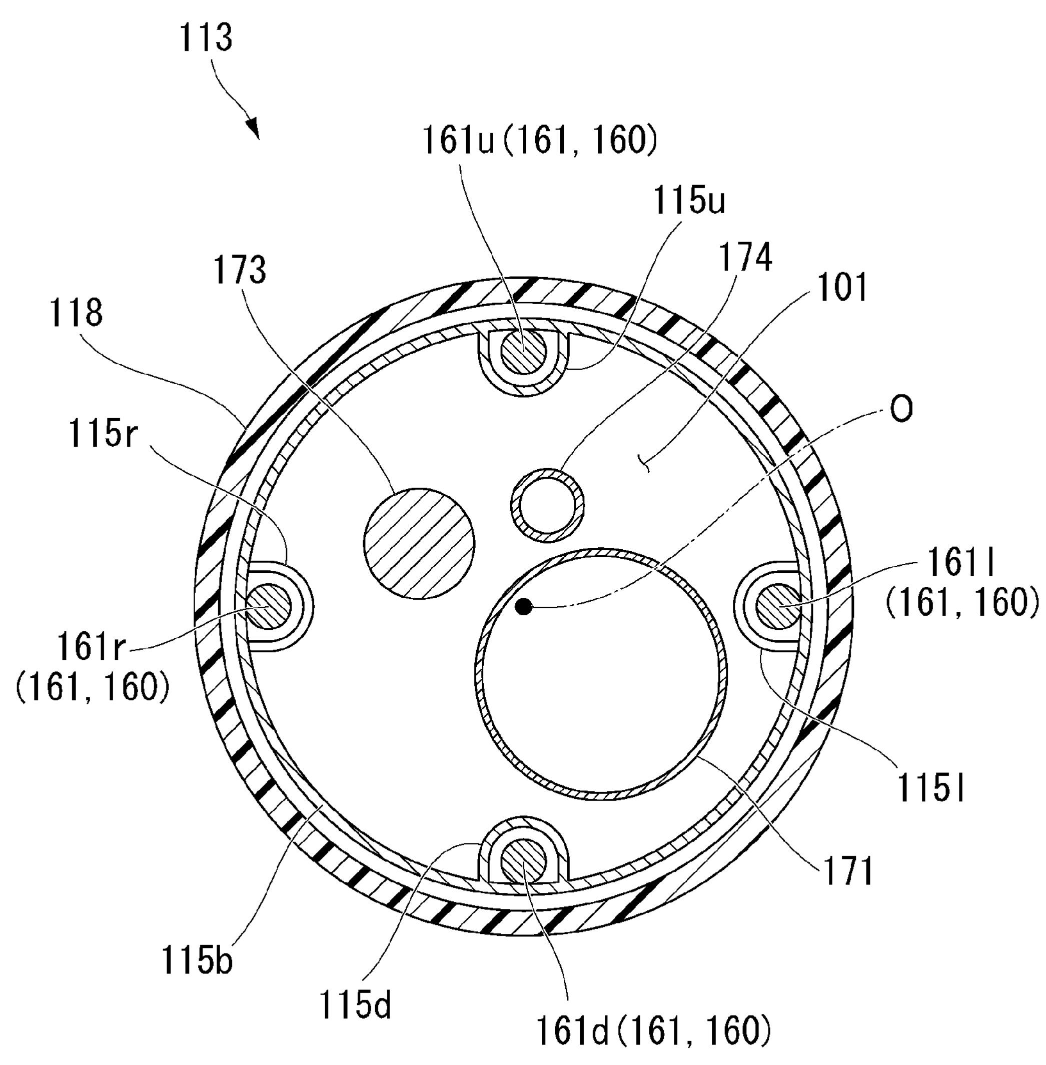
FIG. 4 is a cross-sectional view of the bending portion.
Figure 4:
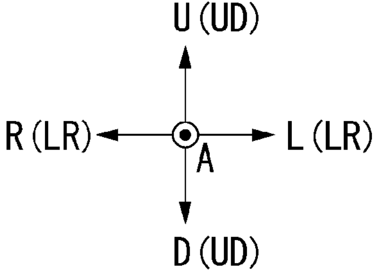

FIG. 4 shows a cross-sectional view of the bending portion 22 along line C1-C1 of FIGS. 2 and 3. On the inner circumferential surface of the second joint ring 115*b*, an upper wire guide 115*u* and a lower wire guide 115*d* are formed. The upper wire guide 115*u* and the lower wire guide 115*d* are arranged on both sides in the upward/downward direction (the UD direction) across the central axis O in the longitudinal direction A. On the inner circumferential surface of the first joint ring 115*a*, a left wire guide 1151 and a right wire guide 115*r* are formed. The left wire guide 1151 and the right wire guide 115*r* are arranged on both sides in the left/right direction (the LR direction) across the central axis O in the longitudinal direction A. Through-holes into which the bending wire 160 is inserted are formed in the upper wire guide 115*u*, the lower wire guide 115*d*, the left wire guide 1151, and the right wire guide 115*r* in the longitudinal direction A.

The second bending portion 114 includes a plurality of joint rings 115 and a second distal end portion 117 connected to the leading joint ring 115. The plurality of joint rings 115 and the second distal end portion 117 are connected inside of the outer sheath 118 in the longitudinal direction A. The second distal end portion 117 is connected to the joint ring 115 of the first bending portion 113 and the joint ring 115 of the proximal end of the second bending portion 114 is attached to the distal end of the intracorporeal soft portion 24. The shapes and number of the joint rings 115 provided in the second bending portion 114 are not limited to the shapes and number of the joint rings 115 shown in FIG. 2.

In the bending portion 22 of the embodiment, the length of the first bending portion 113 in the longitudinal direction A may be shorter than the length of the second bending portion 114 in the longitudinal direction A. Even at the same bending angle, the shorter the bending length, the higher the distal end accuracy. Therefore, by making the length of the first bending portion 113 in the longitudinal direction A shorter than the length of the bending portion of the existing general endoscope in the longitudinal direction, the distal end portion 20 can be moved more accurately. A ratio between the length of the first bending portion 113 in the longitudinal direction A and the length of the second bending portion 114 in the longitudinal direction A may be, for example, in a range of 2:3 to 1:4.

The bending wire 160 is a wire for bending the bending portion 22 and includes a first bending wire 161 for bending the first bending portion 113 and a second bending wire 162 for bending the second bending portion 114. The first bending wire 161 and the second bending wire 162 extend to the connection portion 28*a* through the internal path 101.

Figure 5:
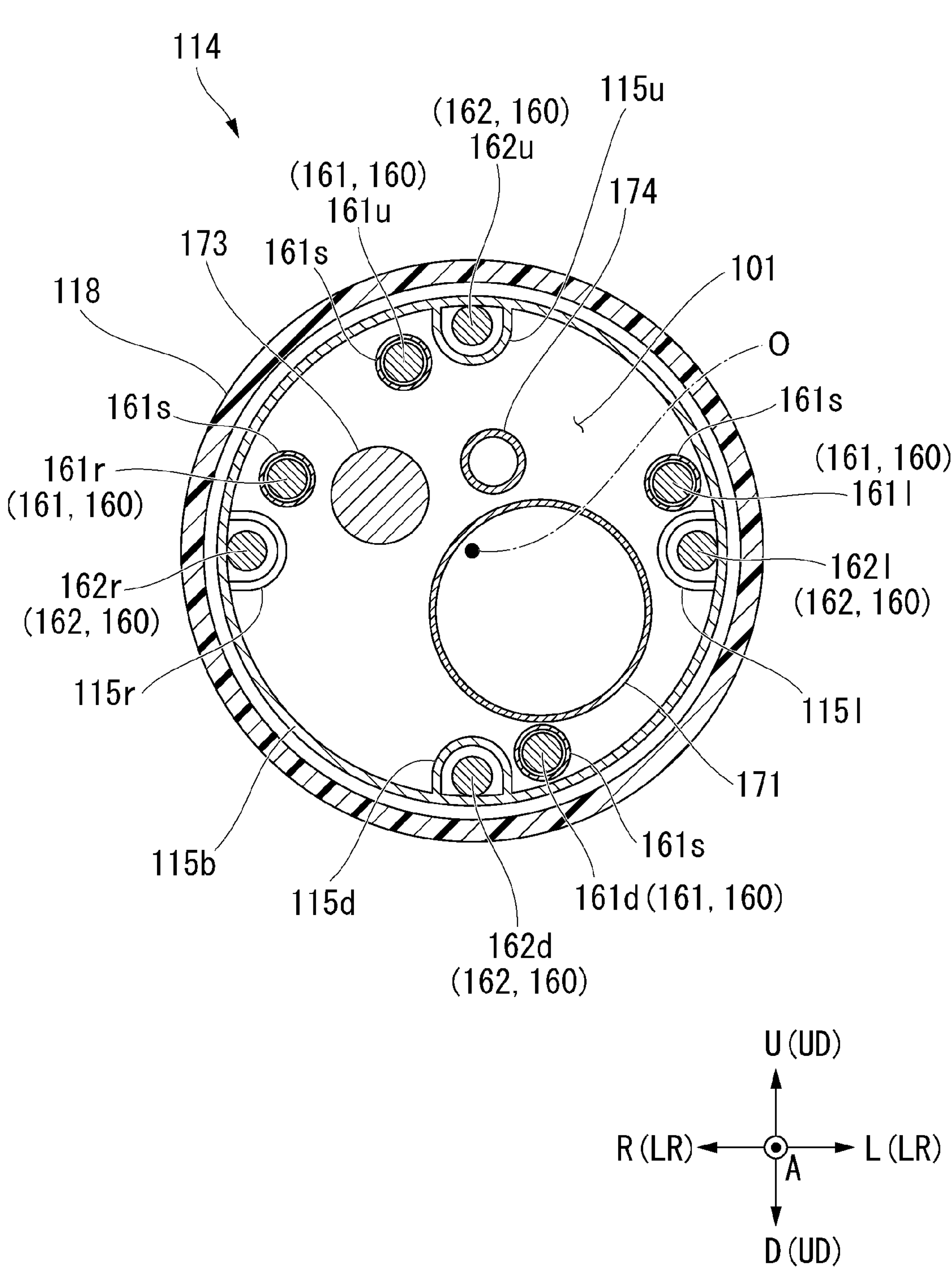
FIG. 5 is a cross-sectional view of a second bending portion.

The first bending wire 161 includes a first upper bending wire 161*u*, a first lower bending wire 161*d*, a first left bending wire 1611, and a first right bending wire 161*r* as shown in FIGS. 2 and 5. The first upper bending wire 161*u*, the first lower bending wire 161*d*, the first left bending wire 1611, and the first right bending wire 161*r* are inserted into the first wire sheath 161*s*. The distal end of the first wire sheath 161*s* is attached to the second distal end portion 117. The first wire sheath 161*s* extends to the connection portion 28*a*.

The first upper bending wire 161*u* and the first lower bending wire 161*d* are wires that bend the first bending portion 113 in the upward/downward direction (the UD direction). As shown in FIG. 4, the first upper bending wire 161*u* is inserted into the upper wire guide 115*u* and the first lower bending wire 161*d* is inserted into the lower wire guide 115*d*. The distal ends of the first upper bending wire 161*u* and the first lower bending wire 161*d* are fixed to the first distal end portion 116 as shown in FIG. 2. The distal ends of the first upper bending wire 161*u* and the first lower bending wire 161*d* fixed to the first distal end portion 116 are arranged on both sides in the upward/downward direction (UD direction) across the central axis O in the longitudinal direction A.

The first left bending wire 1611 and the first right bending wire 161*r* are wires for bending the first bending portion 113 in the left/right direction (LR direction). As shown in FIG. 4, the first left bending wire 1611 is inserted into the left wire guide 1151 and the first right bending wire 161*r* is inserted into the right wire guide 115*r*. The distal ends of the first left bending wire 1611 and the first right bending wire 161*r* are fixed to the first distal end portion 116 as shown in FIG. 2. The distal ends of the first left bending wire 1611 and the first right bending wire 161*r* fixed to the first distal end portion 116 are arranged on both sides in the left/right direction (LR direction) across the central axis O in the longitudinal direction A.

The first bending portion 113 can be bent in a desired direction by pulling or relaxing each of the first bending wires 161 (the first upper bending wire 161*u*, the first lower bending wire 161*d*, the first left bending wire 1611, and the first right bending wire 161*r*).

FIG. 5 shows a cross-sectional view of the second bending portion 114 along line C2-C2 of FIG. 2. The second bending wire 162 has a second upper bending wire 162*u*, a second lower bending wire 162*d*, a second left bending wire 1621, and a second right bending wire 162*r* as shown in FIGS. 2 and 5. Each of the second upper bending wire 162*u*, the second lower bending wire 162*d*, the second left bending wire 1621, and the second right bending wire 162*r* is inserted into the second wire sheath 162*s* as shown in FIG. 2. The distal end of the second wire sheath 162*s* is attached to the joint ring 115 at the proximal end of the second bending portion 114. The second wire sheath 162*s* extends to the connection portion 28*a*.

The second upper bending wire 162*u* and the second lower bending wire 162*d* are wires for bending the second bending portion 114 in the upward/downward direction (UD direction). As shown in FIG. 5, the second upper bending wire 162*u* is inserted into the upper wire guide 115*u* and the second lower bending wire 162*d* is inserted into the lower wire guide 115*d*. The distal ends of the second upper bending wire 162*u* and the second lower bending wire 162*d* are fixed to the second distal end portion 117 as shown in FIG. 2. The distal ends of the second upper bending wire 162*u* and the second lower bending wire 162*d* fixed to the second distal end portion 117 are arranged on both sides in the upward/downward direction (UD direction) across the central axis O in the longitudinal direction A.

The second left bending wire 1621 and the second right bending wire 162*r* are wires for bending the second bending portion 114 in the left/right direction (LR direction). As shown in FIG. 5, the second left bending wire 1621 is inserted into the left wire guide 1151 and the second right bending wire 162*r* is inserted into the right wire guide 115*r*. The distal ends of the second left bending wire 1621 and the second right bending wire 162*r* are fixed to the second distal end portion 117 as shown in FIG. 2. The distal ends of the second left bending wire 1621 and the second right bending wire 162*r* fixed to the second distal end portion 117 are arranged on both sides in the left/right direction (LR direction) across the central axis O in the longitudinal direction A.

The second bending portion 114 can be bent in the desired direction by pulling or relaxing each of the second bending wires 162 (the second upper bending wire 162*u*, the second lower bending wire 162*d*, the second left bending wire 1621, and the second right bending wire 162*r*).

As shown in FIGS. 4 and 5, a bending wire 160, a channel tube 171, an imaging cable 173, and a light guide 174 are inserted into the internal path 101 formed inside of the bending portion 22.

Returning to FIG. 1, the imaging cable 173 and the light guide 174 may be connected to the control device 10 via the connection portion 28*b*. Also, the bending wire 160 and the channel tube 171 may be connected to the drive device 12 via the connection portion 28*a*.

In the embodiment, the connection portion 28*a* includes a first upward/downward bending wire connection portion, a first left/right bending wire connection portion, a second upward/downward bending wire connection portion, and a second left/right bending wire connection portion. The first upward/downward bending wire connection portion is a mechanism for removably connecting wires (the first upper bending wire 161*u* and the first lower bending wire 161*d*) for bending the first bending portion 113 in the upward/downward direction to the drive device 12. The first left/right bending wire connection portion is a mechanism for removably connecting wires (the first left bending wire 1611 and the first right bending wire 161*r*) for bending the first bending portion 113 in the left/right direction to the drive device 12. The second upward/downward bending wire connection portion is a mechanism for removably connecting wires (the second upper bending wire 162*u* and the second lower bending wire 162*d*) for bending the second bending portion 114 in the upward/downward direction to the drive device 12. The second left/right bending wire connection portion is a mechanism for removably connecting wires (the second left bending wire 1621 and the second right bending wire 162*r*) for bending the second bending portion 114 in the left/right direction to the drive device 12. The endoluminal device 2 is connected to the drive device 12 via the connection portion 28*a*, so that the actuator (including at least the electric motor) provided in the drive device 12 can pull or relax the first bending wire 161 and the second bending wire 162 in accordance with the user's manipulation and change a shape of the bending portion 22. Although the bending portion 22 is composed of two first bending portions 113 and a second bending portion 114 in the embodiment, the bending portion 22 may be composed of three or more independent bending portions or may be composed of one bending portion.

The contact detection device 14 is a device that detects the contact of an object and receives the user's input for operating the bending portion 22. The contact detection device 14 may include a touch-sensitive input surface 14*a* for receiving the user input. During an endoscopic examination, the user inserts the endoluminal device 2 into the patient body using one hand and uses the finger of the other hand to input the manipulation to the contact detection device 14. For example, the user may move her or his thumb to input a manipulation to the contact detection device 14 as shown in FIG. 1. The contact detection device 14 is a position information input device that detects a contact point (a touch position) of an object, and may be any of the types of projection type capacitance method, surface type capacitive method, resistive film method, infrared method, and ultrasonic surface elastic wave method. Also, it is only necessary for the contact detection device 14 to have a contact point detection function of an object. The contact detection device 14 may be a type of position information input device using another method.

The contact detection device 14 detects a position on the input surface 14*a* with which the object has come into contact and outputs position information including position coordinates of a contact point to the control device 10. Also, when there is no contact point, i.e., when the object is not in contact with the input surface 14*a*, the contact detection device 14 outputs position information indicating that there is no contact point to the control device 10. The contact detection device 14 may output position information to the control device 10 in prescribed cycles. Also, the contact detection device 14 may include a pressure sensor that detects a pressing force of the object and may output position information including the detected pressing force to the control device 10 as well as the position coordinates of the contact point. Although the contact detection device 14 may detect a region where the object is in contact and output position coordinates representative of the region from the contact region to the control device 10, the contact detection device 14 may output position coordinates indicating a contour of the contact region to the control device 10. Although the contact detection device 14 is equipped with a wireless communication module and transmits position information about the contact point to the control device 10 by establishing a wireless connection with the control device 10 directly or via a wireless repeater, the contact detection device 14 may be connected to the control device 10 using a cable.

The object for touching the input surface 14*a* may be a user's finger, may be a finger with a glove, or may be a touch pen such as a stylus pen. The user may come into contact with the contact detection device 14 with any object. Hereinafter, a case where the user comes into contact with the contact detection device 14 with his or her finger will be described.

Figure 6:
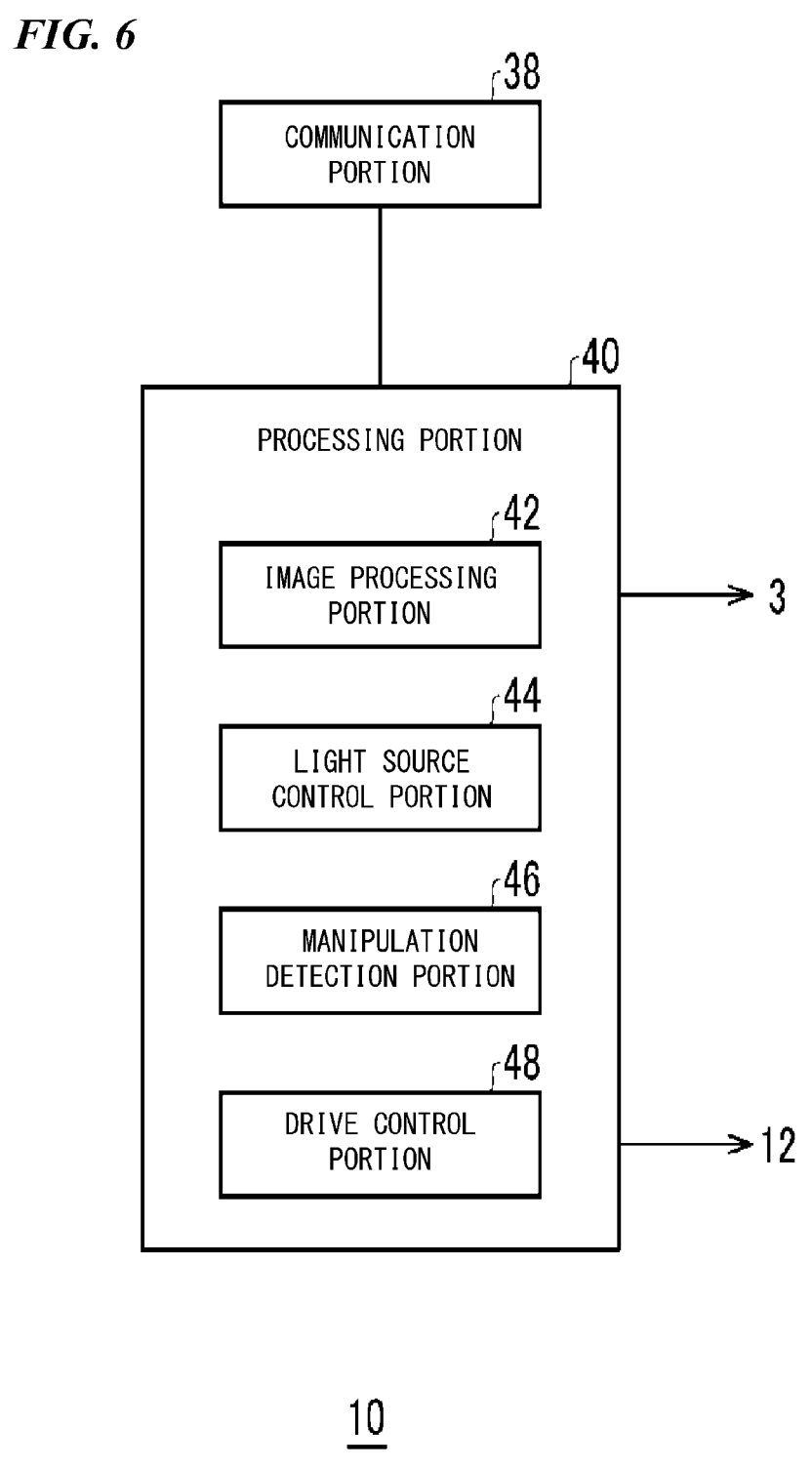

FIG. 6 shows a functional block of the control device 10. The control device includes a communication portion 38 and a processing portion 40 and the processing portion 40 includes an image processing portion 42, a light source control portion 44, a manipulation detection portion 46, and a drive control portion 48. The communication portion 38 is wirelessly connected to the contact detection device 14 and receives position information about the contact point from the contact detection device 14. The manipulation detection portion 46 acquires position information about the contact point received by the communication portion 38 and detects a manipulation input by the user.

The control device 10 includes a computer and various types of functions shown in FIG. 6 are implemented when the computer executes a program. The computer includes hardware such as a memory for loading the program, one or more processors that execute the loaded program, an auxiliary storage device, and other LSI circuits. The processor may include a plurality of electronic circuits including a semiconductor integrated circuit and an LSI circuit and the plurality of electronic circuits may be mounted on one chip or may be mounted on a plurality of chips. The functional blocks shown in FIG. 6 are implemented by hardware and software in cooperation and therefore it will be appreciated by those skilled in the art that these functional blocks can be implemented in various forms by hardware only, software only, or a combination thereof.

The image processing portion 42 generates an endoscopic image by performing image processing on an imaging signal photoelectrically converted in the imaging portion of the endoluminal device 2 and displays the generated endoscopic image on the display device 3 in real-time. The image processing portion 42 may have a function of performing special image processing for the purpose of highlighting and the like in addition to normal image processing such as A/D conversion and noise reduction. The image processing portion 42 has a special image processing function and therefore it is possible to generate an endoscopic image not having undergone special image processing and an endoscopic image having undergone special image processing from an imaging signal obtained in an imaging process using normal light.

The light source control portion 44 supplies illumination light corresponding to an imaging mode to the light guide. The light source control portion 44 may supply special light such as normal light (white light), narrowband light, or excitation light to the light guide in accordance with an observation mode.

The manipulation detection portion 46 identifies a motion of the user's finger from the position information of the contact point and detects the user's manipulation on the basis of the motion of the user's finger. In the embodiment, the manipulation detection portion 46 detects the user's manipulation of changing the shape of the bending portion 22 on the basis of the motion of the user's finger sliding on the input surface 14*a*. Hereinafter, the user's manipulation for changing the shape of the bending portion 22 is referred to as a "bending manipulation (first manipulation)." The drive control portion 48 controls the drive device 12 on the basis of the bending manipulation detected by the manipulation detection portion 46 and performs a shape control process of changing the shape of the bending portion 22. Specifically, the drive control portion 48 causes the drive device 12 to pull or relax each of the first bending wire 161 and the second bending wire 162 and therefore causes the bending portion 22 to bend in a desired direction and at a desired angle.

The manipulation detection portion 46 detects the user's manipulation of maintaining the bent shape of the bending portion 22 on the basis of the motion of the finger while contact with the contact detection device 14 continues after the detection of the bending manipulation starts. Specifically, the manipulation detection portion 46 detects the user's manipulation of maintaining the bent shape of the bending portion 22 on the basis of a motion of pushing the user's finger or a motion of holding the finger stationary for a prescribed period of time or more. Hereinafter, the user's manipulation of maintaining the bent shape of the bending portion 22 is referred to as an "angle lock manipulation (second manipulation)." The drive control portion 48 controls the drive device 12 on the basis of the angle lock manipulation detected by the manipulation detection portion 46 and performs a first control (angle lock control) process of maintaining the shape of the bending portion 22.

Also, in the examination using a conventional non-electric drive endoscope (a type of endoscope that manually bends the bending portion), the user manipulates the angle knob of the endoscope manipulation portion to orient the distal end of the bending portion in a desired direction, and then performs a lock manipulation on an angle fixing lever of the endoscope manipulation portion to maintain (angle-lock) the bent shape of the bending portion, and images a site where there is a lesion using an imaging portion. When the imaging of the lesion is completed and the doctor performs an unlock manipulation on the angle fixing lever, the bent bending portion gradually exhibits behavior to return from the bent shape to the original straight shape due to an elastic force.

Also, in the endoluminal device 2 of the embodiment, because the bending portion 22 is coated with an elastic outer sheath 118 and a tube or sheath is also provided inside thereof, the bent bending portion 22 has an elastic force for returning to a straight shape. However, because the endoluminal device 2 of the embodiment is electrically driven and the first bending wire 161 and the second bending wire 162 have a structure connected to the actuator of the drive device 12, this connection structure provides resistance to the elastic force when the angle lock is unlocked. Therefore, when the angle lock is unlocked, the bent shape of the electrically driven bending portion 22 cannot promptly return to its original straight shape, unlike the non-electric drive bending portion. Therefore, when a user accustomed to a non-electric drive endoscope operation uses the electrically driven endoluminal device 2, the manipulation feeling equivalent to that of a non-electric drive endoscope is preferably given to the user when the angle lock is unlocked.

Hereinafter, a manipulation of bending the bending portion 22 (the bending manipulation or the first manipulation) will be described.

Figure 7:
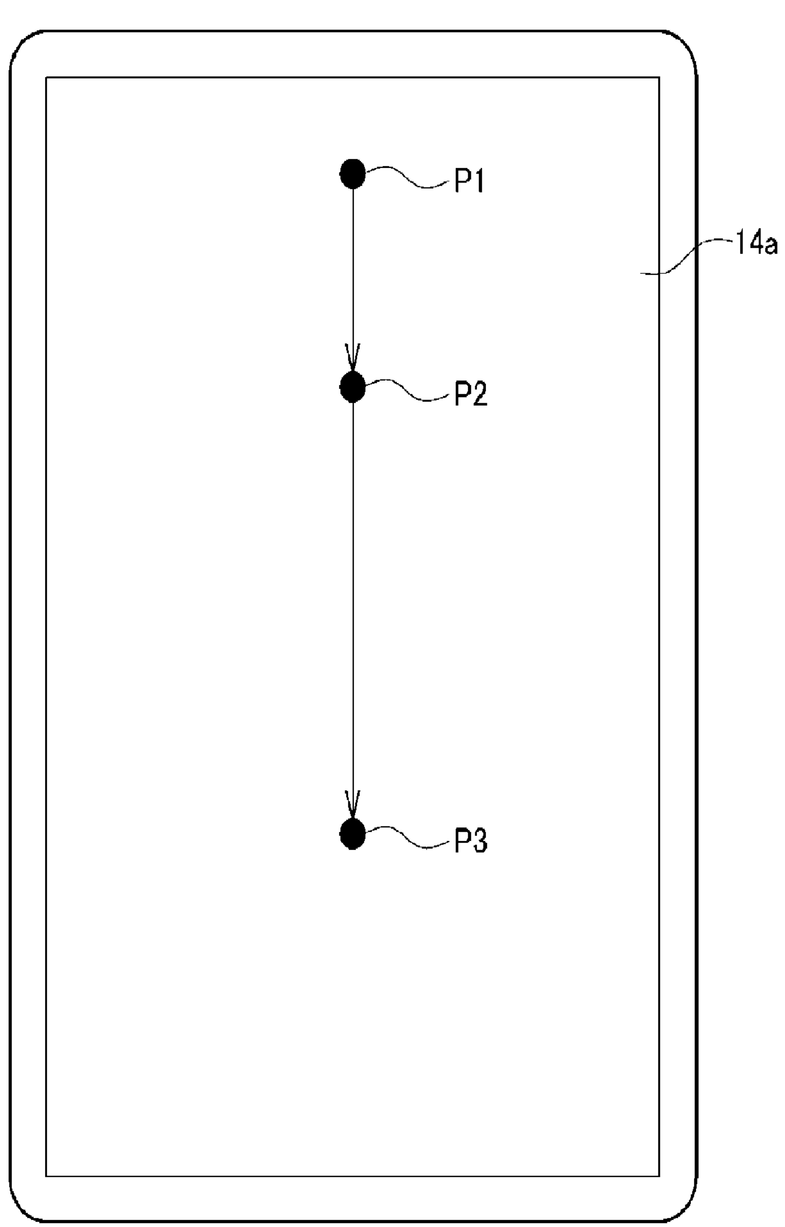
FIG. 7 is a diagram showing a state in which a user's finger moves on an input surface.

FIG. 7 shows a state in which the user's finger in contact with the input surface 14*a* of the contact detection device 14 slides (moves) on the input surface 14*a*. First, the user causes his or her finger to be in contact with the input surface 14*a* at a position P1, and then causes his or her finger to slide to the position P3 in a downward direction. The contact detection device 14 transmits position information of a contact point to the control device 10 periodically (in cycles T). The motion of sliding the finger on the input surface 14*a* in this way may be referred to as a swipe gesture.

In the control device 10, the manipulation detection portion 46 acquires position information (position coordinates) of the contact point. The manipulation detection portion 46 detects that an input of the user is a bending manipulation of changing the shape of the bending portion 22 when contact point positions are continuous in time. The manipulation detection portion 46 may detect that the input of the user is a bending manipulation by determining the contact point positions are continuous in time when two conditions, i.e., (condition 1) that position information including position coordinates is continuously and periodically acquired and (condition 2) that a movement distance in one cycle is less than or equal to a prescribed threshold value, are satisfied.

The manipulation detection portion 46 derives a movement distance and a movement direction of a contact point from time-series contact point position information (position coordinates). Also, the movement distance to be detected may be a movement distance per unit time. In this case, the manipulation detection portion 46 may derive a movement speed of the contact point. The manipulation detection portion 46 notifies the drive control portion 48 that a bending manipulation is being performed and notifies the drive control portion 48 of the movement distance and the movement direction of the contact point. When it is notified that a bending manipulation is being performed, the drive control portion 48 controls the actuator of the drive device 12 on the basis of at least one of the movement distance and the movement direction of the contact point.

Figure 8:
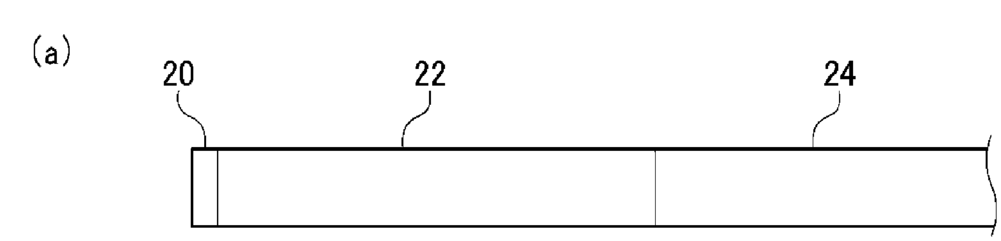
FIG. 8 shows diagrams for describing a state in which a shape of the bending portion changes.
Figure 8:
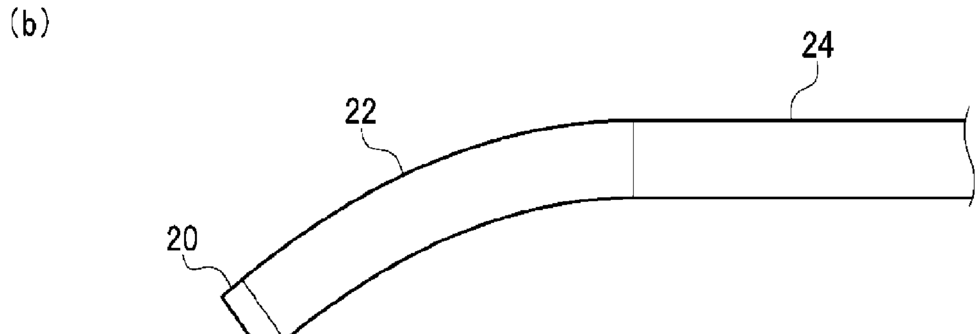
Figure 8:
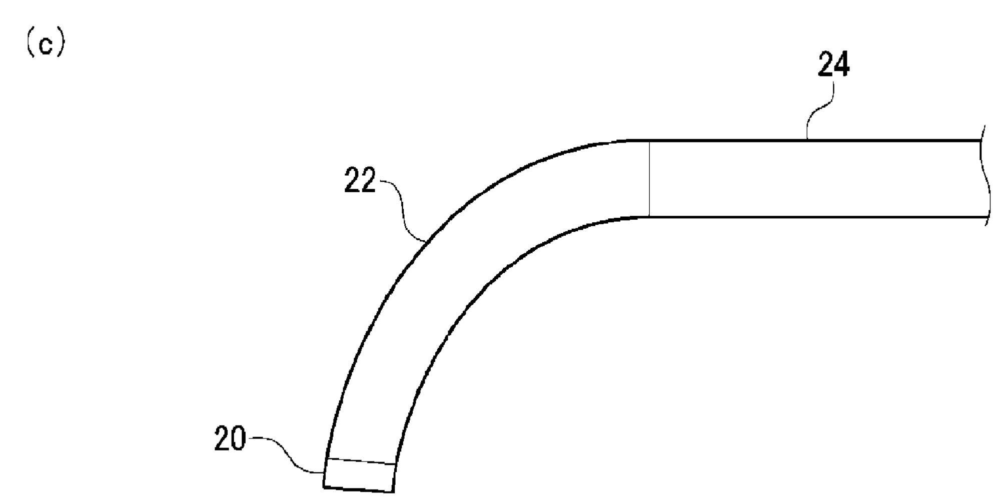

FIGS. 8(*a*) to 8(*c*) are diagrams for describing a state in which a shape of the bending portion 22, which is a part of the endoluminal device 2, changes with the bending manipulation of the user. Also, the movement of the contact point shown in FIG. 7 is performed at a constant speed from a position P1 to a position P3.

FIG. 8(*a*) shows a state in which the bending portion 22 is in a straight shape. The state shown in FIG. 8(*a*) is, for example, a state at the moment when the user's finger comes into contact with the input surface 14*a* at the position P1.

FIG. 8(*b*) shows a state in which the shape of the bending portion 22 has changed. When the contact point moves from the position P1 to the position P2, the drive control portion 48 controls the actuator of the drive device 12 on the basis of the movement distance and the movement direction so that a shape control process of changing the shape of the bending portion 22 is performed. The drive control portion 48 may determine a bending amount (a bending angle) and a bending direction of the bending portion 22 on the basis of the movement distance and the movement direction of the contact point. In the present example, because the movement direction of the contact point is downward, the drive control portion 48 causes the bending portion 22 to bend so that the distal end portion 20 is oriented downward by relaxing the first upper bending wire 161*u* and the second upper bending wire 162*u* and pulling the first lower bending wire 161*d* and the second lower bending wire 162*d*.

FIG. 8(*c*) shows a state in which the shape of the bending portion 22 has further changed. When the contact point moves from the position P2 to the position P3, the drive control portion 48 controls the actuator of the drive device 12 on the basis of the movement distance and the movement direction so that the shape of the bending portion 22 is changed. In the present example, the drive control portion 48 causes the bending portion 22 to bend so that the bending angle becomes larger by further relaxing the first upper bending wire 161*u* and the second upper bending wire 162*u* and further pulling the first lower bending wire 161*d* and the second lower bending wire 162*d* than in the bent state shown in FIG. 8(*b*).

During an endoscopic examination, the user bends the bending portion 22 to orient the imaging portion arranged at the distal end portion 20 toward the lesion and maintains (angle-locks) a bent shape of the bending portion 22 when the lesion is located substantially at the center of the angle of view of the imaging portion. Therefore, preferably, the user easily and quickly performs a manipulation of maintaining the bent shape (an angle lock manipulation) at a desired timing, i.e., a timing when the lesion is located substantially at the center of the angle of view, by performing the bending manipulation while viewing an endoscopic image displayed on the display device 3.

For example, when a manipulation button for inputting an angle lock manipulation is provided on the outer frame of the contact detection device 14, the user can input the angle lock manipulation by pressing the manipulation button after the bending manipulation ends. However, because the user inputs the manipulation to the contact detection device 14 with his or her hand, it is necessary to separate the finger from the input surface 14*a* once after the bending manipulation to press the manipulation button. Therefore, during a period from the time when the finger is separated from the input surface 14*a* to the time when the manipulation button is pressed, the bending portion 22, which is not angle-locked, moves and the angle of view and a positional relationship of the lesion are likely to be misaligned. For this reason, it cannot be said that a manipulation button provided for inputting an angle lock manipulation on the outer frame of the contact detection device 14 is a suitable input means.

Therefore, hereinafter, a method in which the user can perform an angle lock manipulation without separating his or her finger from the input surface 14*a* is proposed.

Example 1

Figure 9:
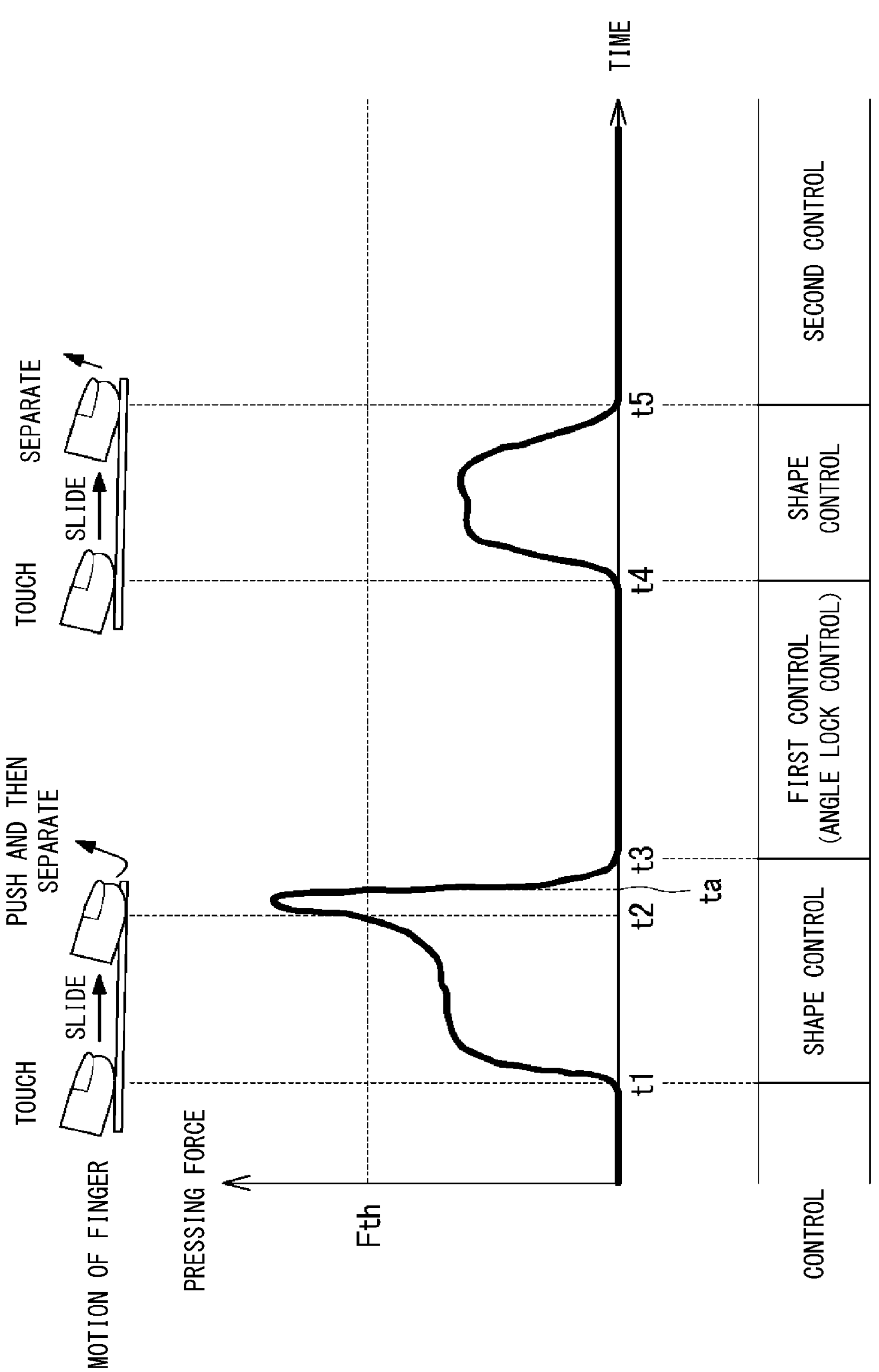
FIG. 9 is a diagram showing a relationship between a motion of the finger and a control process performed by a drive control portion in Example 1.

FIG. 9 shows a relationship between a motion of the finger for the contact detection device 14 and a control process performed by the drive control portion 48 in Example 1. In Example 1, the contact detection device 14 includes a pressure sensor that detects a pressing force with which the finger presses the input surface 14*a*. The contact detection device 14 periodically transmits position information including position coordinates of a contact point and the pressing force by the finger to the control device 10. In Example 1, the angle lock manipulation can be performed by strongly pushing the finger into the input surface 14*a* at a position where the user has ended the motion of the finger and then separating the finger therefrom.

The contact detection device 14 detects the contact of the user's finger at time t1. The manipulation detection portion 46 determines that the contact point positions are continuous in time on the basis of the time-series position information of the contact point during a period from time t1 to time t2 and detects that an input of the user is a bending manipulation of changing the shape of the bending portion 22. The drive control portion 48 controls the drive device 12 on the basis of the bending manipulation detected by the manipulation detection portion 46 and performs a shape control process of changing the shape of the bending portion 22.

At time t2, when the pressing force exceeds a prescribed threshold value Fth, the manipulation detection portion 46 detects the start of the angle lock manipulation of maintaining the bent shape of the bending portion 22. At this point in time, the angle lock manipulation is not yet valid. After the start of the angle lock manipulation, the manipulation detection portion 46 detects the end of the angle lock manipulation at a timing (time t3) when the finger is separated from the input surface 14*a* and recognizes it as a valid angle lock manipulation. That is, the manipulation detection portion 46 detects a valid angle lock manipulation by detecting a pressure change in which the pressing force detected on the input surface 14*a* exceeds the threshold value Fth and the pressing force becomes substantially zero.

Thus, in Example 1, the operation of the finger for the angle lock manipulation is an operation of pushing the finger into the input surface 14*a* so that the pressing force exceeds the prescribed threshold value Fth and then separating the finger from the input surface 14*a*. The motion of the finger for the angle lock manipulation may be referred to as a hold gesture. The user can easily change and maintain the shape of the bending portion 22 by continuously and seamlessly performing a swipe gesture and a hold gesture without separating the finger from the input surface 14*a*. The threshold value Fth may be set for each user. Also, the hold gesture and the swipe gesture may be performed at the same time. For example, a bending manipulation is detected during the swipe when a swipe gesture is performed in a state in which the pressing force exceeds a prescribed threshold value Fth and a valid angle lock manipulation is detected when the finger is separated from the input surface 14*a*.

Even after detecting the start of the angle lock manipulation, the manipulation detection portion 46 continuously detects the bending manipulation because the contact point positions are continuous in time. However, if the position of the finger in contact does not move between the start (time t2) and end (time t3) of the angle lock manipulation (a movement distance is zero), the bent shape of the bending portion 22 does not change. When the finger is separated from the input surface 14*a* at time t3, the manipulation detection portion 46 determines the end of the bending manipulation and detects a valid angle lock manipulation.

Also, the manipulation detection portion 46 may determine whether the angle lock manipulation is valid on the basis of a period from the time when the pressing force falls below the threshold value Fth to the time when the pressing force becomes zero on the condition that the pressing force exceeds the threshold value Fth. In FIG. 9, when the pressing force is below the threshold value Fth at time ta and the pressing force is zero at time t3, but (t3−ta) is less than or equal to a prescribed period of time (for example, 1 sec), the manipulation detection portion 46 may determine that the angle lock manipulation is valid. In this case, if (t3−ta) exceeds the prescribed period of time, the manipulation detection portion 46 may determine that the angle lock manipulation is invalid.

When the angle lock manipulation is detected, the drive control portion 48 controls the drive device 12 so that a first control (angle lock control) process of maintaining the changed shape of the bending portion 22 is performed. The drive control portion 48 may control the drive device 12 so that the shape of the bending portion 22 is maintained when the bending manipulation ends or when a valid angle lock manipulation is detected. The drive control portion 48 may perform the first control process using the following method.

(1) Bending Angle Control Method

The drive control portion 48 estimates the bending angle of the bending portion 22 at the start of the angle lock from the tension of each of the first bending wire 161 and the second bending wire 162. The drive control portion 48 performs a control process of maintaining the bending angle of the bending portion 22 by maintaining the tension of each of the first bending wire 161 and the second bending wire 162.

(2) Motor Angle Control Method

The drive control portion 48 stores the motor angle of the drive device 12 at the start of the angle lock and performs a control process of maintaining the bending angle of the bending portion 22 by maintaining the motor angle.

(3) Motor Lock Control Method

The drive control portion 48 maintains the bending angle of the bending portion 22 by short-circuiting the motor terminals in the drive device 12 and braking the motor when the angle lock starts.

The drive control portion 48 may employ any one of the above methods or other methods to maintain the bent shape of the bending portion 22.

The angle lock state may be eliminated at the moment when the user's finger comes into contact with the input surface 14*a*. That is, while the drive control portion 48 is executing the first control (angle lock control) process, the drive control portion 48 may promptly stop executing the first control process if the manipulation detection portion 46 acquires position information including the position coordinates of the contact point from the contact detection device 14.

The contact detection device 14 detects the contact of the user's finger at time t4. At this moment, the drive control portion 48 promptly stops the first control process. The manipulation detection portion 46 determines that the contact point positions are continuous in time on the basis of the time-series position information of the contact point between time t4 and time t5 and detects that the user's input is a bending manipulation. The drive control portion 48 controls the drive device 12 on the basis of the bending manipulation detected by the manipulation detection portion 46 and performs a shape control process of changing the shape of the bending portion 22.

The manipulation detection portion 46 does not detect the angle lock manipulation after detecting a bending manipulation on the basis of the time-series position information of the contact point after time t4 and the drive control portion 48 ends the shape control process at time t5 and then performs the second control process different from the first control process when the bending manipulation ends. Hereinafter, specific examples of the second control process are shown.

(a) Straightening Control

The drive control portion 48 performs a control process so that the bent bending portion 22 returns to a straight shape. For example, as shown in FIGS. 8(*b*) and 8(*c*), when the distal end portion 20 is oriented downward and the bending portion 22 is bent, the first upper bending wire 161*u* and the second upper bending wire 162*u* are relaxed and the first lower bending wire 161*d* and the second lower bending wire 162*d* are pulled. Therefore, the drive control portion 48 pulls the first upper bending wire 161*u* and the second upper bending wire 162*u* and relaxes the first lower bending wire 161*d* and the second lower bending wire 162*d* so that the bending portion 22 has a straight shape. When the drive control portion 48 performs straightening control, the bending portion 22 can provide behavior in which the bending portion 22 returns from the bent shape to the straight shape to the user who has ended the bending manipulation.

(b) Straightening Control+External Force Monitoring

The drive control portion 48 stops straightening control when an external force acts on the bending portion 22 while performing a control process so that the bent bending portion 22 returns to the straight shape. In this case, the endoluminal device 2 or the drive device 12 may have an external force sensor that detects the external force acting on the bending portion 22. For example, an aspect of the external force sensor may be a plurality of pressure-sensitive sensors provided on the surface or inside of the bending portion 22.

When an external force has acted on the bending portion 22, the drive control portion 48 can prevent an excessive force from being applied to the lumen by immediately stopping the straightening control. At this time, the drive control portion 48 may perform the second control process so that the shape of the bending portion 22 is maintained when an external force is detected. When the external force sensor detects that no external force is acting, the drive control portion 48 may resume the straightening control.

(c) Wire-Free Control

The drive control portion 48 ensures that the movement of the bending portion 22 is not constrained by the bending wire 160 connected to the bending portion 22, so that the bending portion 22 can change its shape in accordance with an external force. For example, the drive control portion 48 shortens the wire path length and sufficiently relaxes all the bending wires 160, thereby releasing the movement constraint of the bending portion 22 by the bending wire 160. For example, when the bending wire 160 is connected to the bending portion 22 via a pulley, the drive control portion 48 may shorten the wire path length by shifting the position of the pulley.

Also, when a traction device of the bending wire 160 is connected to the motor via an electric clutch, the drive control portion 48 cuts off the power transmission by the electric clutch so that the bending wire 160 can move freely. Also, the drive control portion 48 may open the electric circuit of the motor so that the motor can be passively rotated so that the bending wire 160 can move freely. When the drive control portion 48 executes wire-free control, the bent bending portion 22 can return to its original straight shape due to its elastic force without being constrained by the bending wire 160.

As described above, when the manipulation detection portion 46 does not detect the angle lock manipulation between the start and the end of the bending manipulation, the drive control portion 48 may perform a second control process different from the angle lock control process to return the bent bending portion 22 to its original straight shape. The second control process to be performed may be any of (a) to (c), but may be another control process. For example, the endoluminal device 2 or the drive device 12 has an external force sensor that detects an external force acting on the bending portion 22 and the drive control portion 48 may control the shape of the bending portion 22 in accordance with a magnitude and a direction of an external force detected by the external force sensor. At this time, when the external force is applied to the bending portion 22, the drive control portion 48 may estimate the shape of the bending portion 22 deformed by the external force and control the shape of the bending portion 22 so that the shape becomes the estimated shape.

Figure 10:
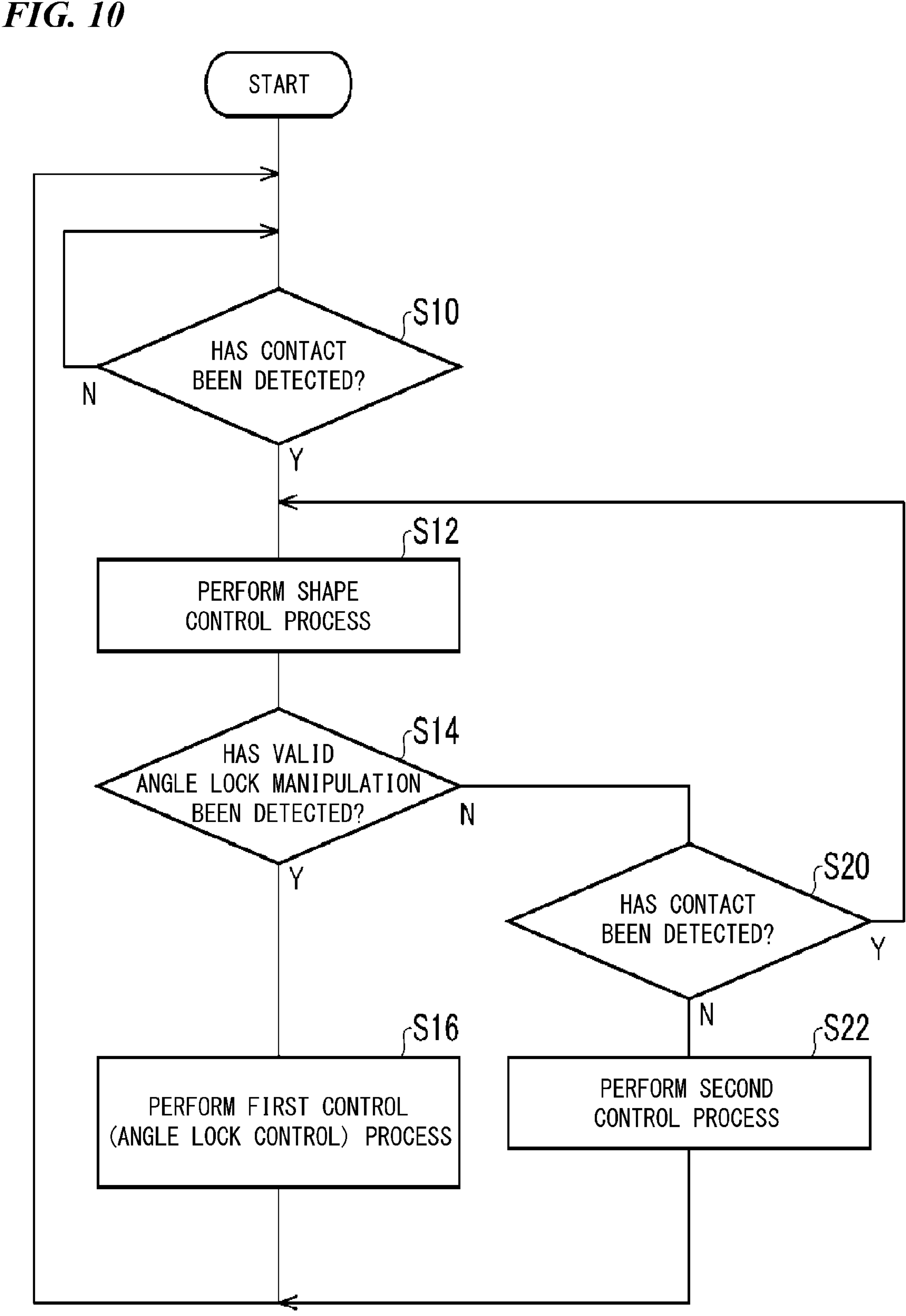
FIG. 10 is a diagram showing a flowchart for controlling an operation of the bending portion.

FIG. 10 shows a flowchart for controlling the operation of the bending portion 22. The manipulation detection portion 46 acquires contact information of the user's finger from the contact detection device 14 and monitors the presence or absence of contact (S10). When the manipulation detection portion 46 detects the contact of the user's finger (Y in S10), the manipulation detection portion 46 acquires position information from the contact detection device 14 in a time series and detects the bending manipulation. The drive control portion 48 performs a shape control process of changing the shape of at least a part of the endoluminal device 2 on the basis of the bending manipulation (S12). Also, when there is no change in the contact position, the drive control portion 48 executes a shape control process having a control amount of 0, and the shape does not substantially change. In the embodiment, the drive control portion 48 may control the bending angle of the bending portion 22.

When the manipulation detection portion 46 detects a valid angle lock manipulation (Y in S14), the drive control portion 48 performs a first control (angle lock control) process of maintaining the shape of the bending portion 22. Thus, according to the embodiment, the user can input a bending manipulation and an angle lock manipulation in a seamless motion. While the manipulation detection portion 46 detects the contact of the user's finger (N in S10), the drive control portion 48 continuously performs the first control process. When the manipulation detection portion 46 detects the contact of the user's finger (Y in S10), the drive control portion 48 ends the first control process and performs the shape control process (S12).

In S14, when the manipulation detection portion 46 has not detected a valid angle lock manipulation (N in S14) and is continuously detecting contact with the user's finger (Y in S20), the drive control portion 48 continuously performs the shape control process (S12). On the other hand, when the manipulation detection portion 46 no longer detects the contact of the user's finger (N in S20), the drive control portion 48 ends the shape control process and executes the second control process (S22). The drive control portion 48 continuously performs the second control process while the manipulation detection portion 46 detects the contact of the user's finger (N in S10). When the manipulation detection portion 46 detects the contact of the user's finger (Y in S10), the drive control portion 48 ends the second control process and performs the shape control process (S12).

Example 2

Figure 11:
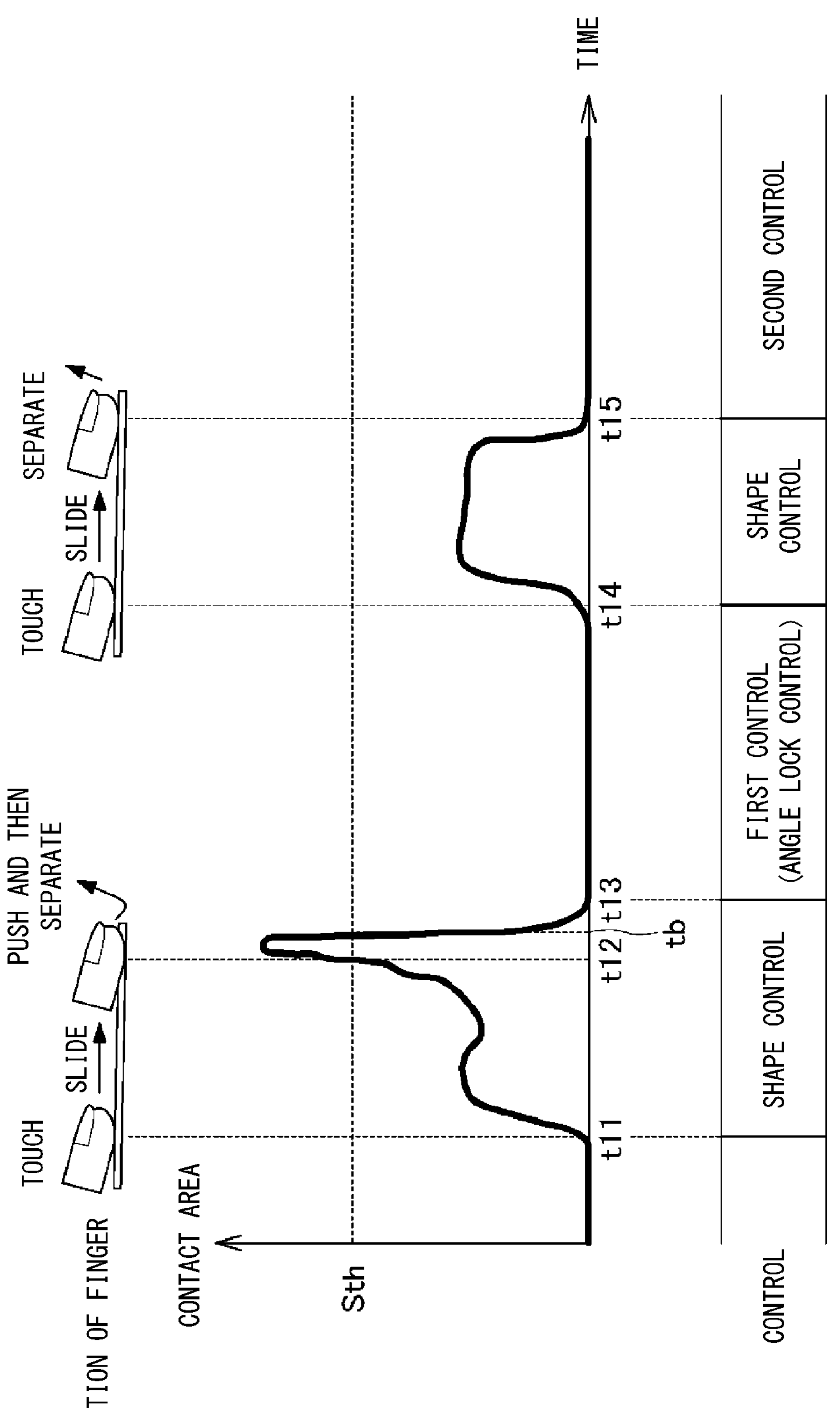
FIG. 11 is a diagram showing a relationship between a motion of the finger and a control process performed by the drive control portion in Example 2.

FIG. 11 shows a relationship between a motion of the finger for the contact detection device 14 and a control process performed by the drive control portion 48 in Example 2. In Example 2, the contact detection device 14 has a function of deriving an area in which the finger comes into contact with the input surface 14*a*. The contact detection device 14 periodically transmits position information including the position coordinates of the contact point and the contact area of the finger to the control device 10. In Example 2, an angle lock manipulation can be performed by pushing a finger into the input surface 14*a* at a position where the user has ended the motion of the finger and then separating the finger therefrom.

The contact detection device 14 detects the contact of the user's finger at time t11. The manipulation detection portion 46 determines that the contact point positions are continuous in time on the basis of the time-series position information of the contact point during a period from time t11 to time t12 and detects that the user's input is a bending manipulation. The drive control portion 48 controls the drive device 12 on the basis of the bending manipulation detected by the manipulation detection portion 46 and performs the shape control process of changing the shape of the bending portion 22.

At time t12, when the contact area exceeds a prescribed threshold value Sth, the manipulation detection portion 46 detects the start of the angle lock manipulation of maintaining the bent shape of the bending portion 22. At this point in time, the angle lock manipulation is not yet valid. After the start of the angle lock manipulation, the manipulation detection portion 46 detects the end of the angle lock manipulation at a timing (time t13) when the finger is separated from the input surface 14*a* and recognizes it as a valid angle lock manipulation. That is, the manipulation detection portion 46 detects a valid angle lock manipulation by detecting an area change in which the contact area of the finger exceeds the threshold value Sth and the contact area becomes substantially zero. When a valid angle lock manipulation is detected, the drive control portion 48 starts the angle lock control process.

Thus, in Example 2, the operation of the finger for the angle lock manipulation is an operation of pushing the finger into the input surface 14*a* so that the contact area exceeds the prescribed threshold value Sth and then separating the finger from the input surface 14*a*. The user can easily change and maintain the shape of the bending portion 22 by continuously and seamlessly performing a swipe gesture and a hold gesture without separating the finger from the input surface 14*a*. The threshold value Sth may be set for each user.

Even after detecting the start of the angle lock manipulation, the manipulation detection portion 46 continuously detects the bending manipulation because the contact point positions are continuous in time. However, if the position of the finger in contact does not move between the start and end of the angle lock manipulation (a movement distance is zero), the bent shape of the bending portion 22 does not change. When the finger is separated from the input surface 14*a* at time t13, the manipulation detection portion 46 determines the end of the bending manipulation and detects a valid angle lock manipulation.

Also, the manipulation detection portion 46 may determine whether the angle lock manipulation is valid on the basis of a period from the time when the contact area falls below the threshold value Sth to the time when the pressing force becomes zero on the condition that the contact area exceeds the threshold value Sth. In FIG. 11, when the contact area is below the threshold value Sth at time tb and the contact area is zero at time t13, but (t13−tb) is less than or equal to a prescribed period of time (for example, 1 sec), the manipulation detection portion 46 may determine that the angle lock manipulation is valid.

The contact detection device 14 detects the contact of the user's finger at time t14. The manipulation detection portion 46 determines that the contact point positions are continuous in time on the basis of the time-series position information of the contact point during a period from time t14 to time t15 and detects that the user's input is a bending manipulation. The drive control portion 48 controls the drive device 12 on the basis of the bending manipulation detected by the manipulation detection portion 46 and performs the shape control process of changing the shape of the bending portion 22.

The manipulation detection portion 46 does not detect the angle lock manipulation after detecting a bending manipulation on the basis of the time-series position information of the contact point after time t14 and the drive control portion 48 may end the shape control process at time t15 and then perform the second control process different from the first control process when the bending manipulation ends. That is, when the manipulation detection portion 46 does not detect the angle lock manipulation between the start and end of the bending operation, the drive control portion 48 may perform the above-described second control process.

Example 3

Figure 12:
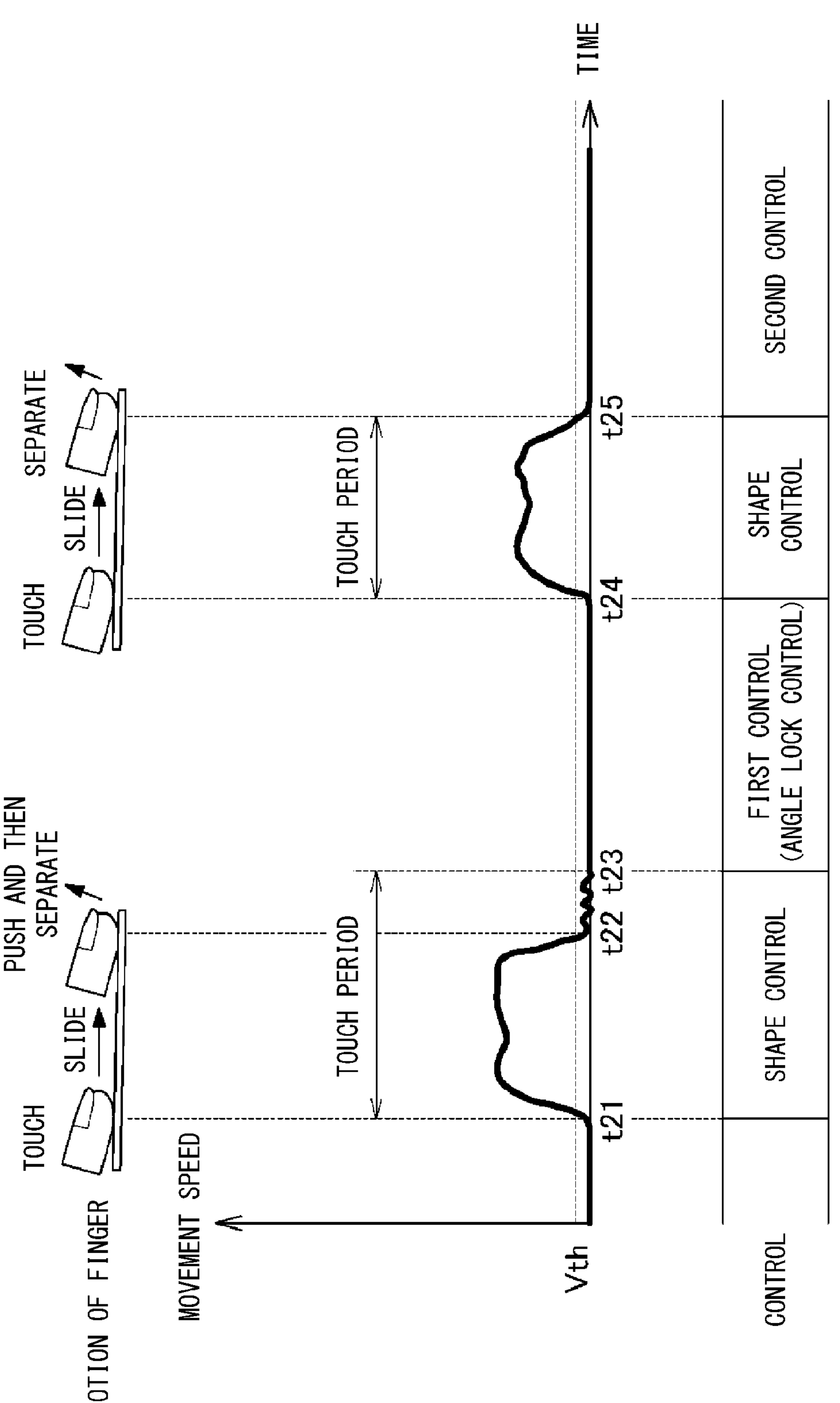
FIG. 12 is a diagram showing the relationship between a motion of the finger and a control process performed by the drive control portion in Example 3.

FIG. 12 shows a relationship between a motion of the finger for the contact detection device 14 and the control process performed by the drive control portion 48 in Example 3. The contact detection device 14 in Example 3 may not have a pressure detection function or a contact area measurement function. The contact detection device 14 periodically transmits position information of a contact point to the control device 10 and the manipulation detection portion 46 derives a movement speed of the contact point in real time. In Example 3, an angle lock manipulation can be performed by performing a hold gesture to hold the motion of the finger stationary for a prescribed period of time or more at a position where the user has ended the motion of the finger and then separate the finger therefrom.

The contact detection device 14 detects the contact of the user's finger at time t21. The manipulation detection portion 46 determines that the contact point positions are continuous in time on the basis of the time-series position information of the contact point during a period from time t21 to time t22 and detects that the user's input is a bending manipulation. The drive control portion 48 controls the drive device 12 on the basis of the bending manipulation detected by the manipulation detection portion 46 and performs the shape control process of changing the shape of the bending portion 22.

At time t22, when the movement speed of the contact point falls below a prescribed threshold value Vth, the manipulation detection portion 46 detects the start of an angle lock manipulation of maintaining the bent shape of the bending portion 22. At this point in time, the angle lock manipulation is not yet valid. After the start of the angle lock manipulation, the manipulation detection portion 46 detects the end of the angle lock manipulation at a timing (time t23) when the finger is separated from the input surface 14*a* and recognizes it as a valid angle lock manipulation. The manipulation detection portion 46 detects the valid angle lock manipulation by detecting that the finger is separated from the input surface 14*a* after a period in which the movement speed of the finger is less than Vth is greater than or equal to a prescribed period of time and the drive control portion 48 starts the angle lock control process. The threshold value Vth is set to a value for determining that the finger is substantially stationary and a prescribed period of time for determining a stationary state may be, for example, about 2 sec.

Thus, in Example 3, a finger operation for the angle lock manipulation is an operation of separating the finger from the input surface 14*a* after the finger is stationary on the input surface 14*a* for a prescribed period of time or more. The user can easily change and maintain the shape of the bending portion 22 by continuously and seamlessly performing a swipe gesture and a hold gesture without separating the finger from the input surface 14*a*.

Even after detecting the start of the angle lock manipulation, the manipulation detection portion 46 continuously detects the bending manipulation because the contact point positions are continuous in time. However, in Example 3, because the position of the finger in contact does not move (the movement speed is substantially zero) between the start and end of the angle lock manipulation, the bent shape of the bending portion 22 does not change. When the finger is separated from the input surface 14*a* at time t23, the manipulation detection portion 46 determines the end of the bending manipulation and detects a valid angle lock manipulation.

The contact detection device 14 detects the contact of the user's finger at time t24. The manipulation detection portion 46 determines that contact point positions are continuous in time on the basis of time-series position information of a contact point between time t24 and time t25 and detects that the user's input is a bending manipulation. The drive control portion 48 controls the drive device 12 on the basis of the bending manipulation detected by the manipulation detection portion 46 and performs the shape control process of changing the shape of the bending portion 22.

The manipulation detection portion 46 does not detect the angle lock manipulation after detecting a bending manipulation on the basis of the time-series position information of the contact point after time t24 and the drive control portion 48 may end the shape control process at time t25 and then perform the second control process different from the first control process when the bending manipulation ends. That is, when the manipulation detection portion 46 does not detect the angle lock manipulation between the start and end of the bending manipulation, the drive control portion 48 may perform the above-described second control process.

The present disclosure has been described above on the basis of a plurality of examples. These embodiments and examples are illustrative and it will be appreciated by those skilled in the art that various modified examples for combinations of constituent elements or processing processes thereof are possible and such modified examples are also within the scope of the present disclosure. Although the bending portion 22 includes two first bending portions 113 and a second bending portion 114 in the embodiment, it may be composed of one bending portion or may be composed of three or more bending portions.

The present invention can be applied to a medical system that observes and treats luminal organs and the like.

What is claimed is:

1. An endoluminal device system comprising:

an endoluminal device configured to be inserted into a lumen;

a contact detection device configured to detect contact of an object; and one or more processors having hardware, wherein the one or more processors are configured to:

in response to a first detection by the contact detection device of a first motion of the object in contact with the contact detection device, determine that a user performed a first manipulation;

in response to determining that the user performed the first manipulation, perform a shape control process of controlling a drive device to change a shape of at least a part of the endoluminal device;

in response to a second detection by the contact detection device of a second motion of the object while the object is continuously in contact with the contact detection device after the first manipulation starts, determine that the user performed a second manipulation; and in response to determining that the user performed the second manipulation, perform a first control process of controlling the drive device to maintain the changed shape of the at least a part of the endoluminal device.

2. The endoluminal device system according to claim 1, wherein the one or more processors are configured to perform a second control process different from the first control process when the first manipulation ends without the second manipulation being detected after the detection of the first manipulation starts.

3. The endoluminal device system according to claim 1, wherein the one or more processors are configured to perform the first control process of controlling the drive device to maintain the changed shape of the at least the part of the endoluminal device when the first manipulation ends or when the second manipulation is detected.

4. The endoluminal device system according to claim 1, wherein the endoluminal device includes a bending portion whose shape can be changed and a soft portion connected to a proximal end of the bending portion, and wherein the one or more processors are configured to perform the first control process of controlling the drive device to maintain the changed shape in which the bending portion is bent.

5. The endoluminal device system according to claim 2, wherein the endoluminal device includes a bending portion whose shape can be changed and a soft portion connected to a proximal end of the bending portion, and wherein the one or more processors are configured to perform the second control process of controlling the drive device to change the shape of the bending portion in accordance with an external force.

6. The endoluminal device system according to claim 2, wherein the endoluminal device includes a bending portion whose shape can be changed and a soft portion connected to a proximal end of the bending portion, and wherein the one or more processors are configured to perform the second control process of controlling the drive device to return the bending portion to a straight shape.

7. The endoluminal device system according to claim 6, further comprising an external force sensor configured to detect an external force acting on the bending portion, wherein the one or more processors are configured to perform the second control process so that a shape of the bending portion at a point in time when the external force has been detected is maintained if the external force sensor detects the external force.

8. The endoluminal device system according to claim 2, further comprising an external force sensor configured to detect an external force acting on the endoluminal device, wherein the one or more processors are configured to perform the second control process of controlling the drive device to control a shape of at least a part of the endoluminal device in accordance with a magnitude and a direction of the external force detected by the external force sensor.

9. The endoluminal device system according to claim 2, wherein the one or more processors are configured to:

detect the first manipulation on the basis of a motion of sliding the object; and detect the second manipulation on the basis of a motion of pushing the object or a motion of causing the object to be stationary for a prescribed period of time.

10. The endoluminal device system according to claim 9, wherein the one or more processors are configured to:

detect a movement distance and a movement direction of a contact point of the object; and perform the shape control process of controlling the drive device to change the shape of at least the part of the endoluminal device on the basis of at least one of the movement distance and the movement direction.

11. The endoluminal device system according to claim 2, wherein the contact detection device includes a pressure sensor configured to detect a pressing force of the object, and wherein the one or more processors are configured to detect the second manipulation process on the basis of the pressing force detected by the pressure sensor.

12. The endoluminal device system according to claim 10, wherein the one or more processors are configured to detect the second manipulation process on the basis of an area of a contact point of the object or a movement speed of the contact point.

13. A control method of controlling an endoluminal device in an endoluminal device system including the endoluminal device configured to be inserted into a lumen and a contact detection device configured to detect contact of an object, the control method comprising:

in response to a first detection by the contact detection device of a first motion of the object in contact with the contact detection device, determining that a user performed a first manipulation;

in response to determining that the user performed the first manipulation, performing a shape control process of controlling a drive device to change a shape of at least a part of the endoluminal device;

in response to a second detection by the contact detection device of a second motion of the object while the object is continuously in contact with the contact detection device after the first manipulation starts, determining that the user performed a second manipulation; and in response to determining that the user performed the second manipulation, performing a first control process of controlling the drive device to maintain the changed shape of the at least a part of the endoluminal device.

14. The control method of controlling the endoluminal device according to claim 13, comprising performing a second control process different from the first control process when the first manipulation ends without the second manipulation being detected after the detection of the first manipulation starts.

15. The control method of controlling the endoluminal device according to claim 13, comprising performing the first control process of controlling the drive device to maintain the changed shape of the at least the part of the endoluminal device when the first manipulation ends or when the second manipulation is detected.

16. The control method of controlling the endoluminal device according to claim 13, wherein the endoluminal device includes a bending portion whose shape can be changed and a soft portion connected to a proximal end of the bending portion, and wherein performing the first control process comprises controlling the drive device to maintain the changed shape in which the bending portion is bent.

17. A non-transitory computer-readable storage medium storing a program for controlling an endoluminal device in an endoluminal device system including the endoluminal device configured to be inserted into a lumen and a contact detection device configured to detect contact of an object, the program causing a computer to at least:

in response to a first detection by the contact detection device of a first motion of an object in contact with a contact detection device, determine that a user performed a first manipulation;

in response to determining that the user performed the first manipulation, perform a shape control process of controlling a drive device to change a shape of at least a part of the endoluminal device;

in response to a second detection by the contact detection device of a second motion of the object while the object is continuously in contact with the contact detection device after the first manipulation starts, determine that the user performed a second manipulation; and in response to determining that the user performed the second manipulation, perform a first control process of controlling the drive device to maintain the changed shape of the at least a part of the endoluminal device.

18. The non-transitory computer-readable storage medium according to claim 17, wherein the program causes the computer to perform a second control process different from the first control process when the first manipulation ends without the second manipulation being detected after the detection of the first manipulation starts.

19. The non-transitory computer-readable storage medium according to claim 17, wherein the program causes the computer to perform the first control process of maintaining the changed shape of the at least the part of the endoluminal device when the first manipulation ends or when the second manipulation is detected.

20. The non-transitory computer-readable storage medium according to claim 17, wherein the endoluminal device includes a bending portion whose shape can be changed and a soft portion connected to a proximal end of the bending portion, and wherein the program causes the computer to perform the first control process of controlling the drive device to maintain the changed shape in which the bending portion is bent.

* * * * *